(12) United States Patent
Unal et al.

(10) Patent No.: US 12,740,876 B2
(45) Date of Patent: Sep. 22, 2026

(54) 3 DEGREES OF FREEDOM ANKLE PROSTHESIS

(71) Applicant: OZYEGIN UNIVERSITESI, Istanbul (TR)

(72) Inventors: Ramazan Unal, Istanbul (TR); Baris Baysal, Istanbul (TR)

(73) Assignee: OZYEGIN UNIVERSITES!, Istanbul (TR)

( * ) Notice: Subject to any disclaimer, the term of this patent is extended or adjusted under 35 U.S.C. 154(b) by 726 days.

(21) Appl. No.: 18/034,392

(22) PCT Filed: Dec. 30, 2021

(86) PCT No.: PCT/TR2021/051642
§ 371 (c)(1),
(2) Date: Apr. 28, 2023

(87) PCT Pub. No.: WO2022/146400
PCT Pub. Date: Jul. 7, 2022

(65) Prior Publication Data

US 2023/0390085 A1 Dec. 7, 2023

(30) Foreign Application Priority Data

Dec. 30, 2020 (TR) ................................ 2020/22500

(51) Int. Cl.
*A61F 2/66* (2006.01)
*A61F 2/50* (2006.01)

(52) U.S. Cl.
CPC .... *A61F 2/6607* (2013.01); *A61F 2002/5081* (2013.01); *A61F 2002/6614* (2013.01)

(58) Field of Classification Search
CPC .... A61F 2/6607; A61F 2002/6614–2002/6692
See application file for complete search history.

(56) References Cited

U.S. PATENT DOCUMENTS

| | | | | |
|---|---|---|---|---|
| 5,425,780 | A | 6/1995 | Flatt et al. | |
| 10,806,602 | B2 * | 10/2020 | Rouse | A61B 5/1038 |
| 2006/0249315 | A1 | 11/2006 | Herr et al. | |
| 2019/0307583 | A1 | 10/2019 | Herr et al. | |

(Continued)

FOREIGN PATENT DOCUMENTS

| | | | | |
|---|---|---|---|---|
| CN | 102973338 | A | 3/2013 | |
| CN | 110074905 | B * | 10/2020 | A61F 2/6607 |

(Continued)

OTHER PUBLICATIONS

R. Unal, et al., Towards a Fully Passive Transfemoral Prosthesis for Normal Walking, The Fourth IEEE RAS/EMBS International Conference on Biomedical Robotics and Biomechatronics, 2012, pp. 1949-1954.

*Primary Examiner* — Alvin J Stewart
(74) *Attorney, Agent, or Firm* — Bayramoglu Law Offices LLC

(57) ABSTRACT

An ankle prosthesis or orthosis includes a tibia portion, at least one foot clamping member, at least one upper foot part, at least one lower foot part, at least a first piston, at least a second piston, which allows that internal rotational movement, inversion and eversion of the ankle joints and alignment thereof with a below-knee mechanism at 0 degrees are performed in an efficient manner is disclosed.

20 Claims, 6 Drawing Sheets

(56) References Cited

U.S. PATENT DOCUMENTS

| | | | | |
|---|---|---|---|---|
| 2023/0126674 | A1* | 4/2023 | Hansen | A61F 2/6607 623/52 |
| 2023/0225884 | A1* | 7/2023 | Unal | A61F 2/64 623/24 |
| 2024/0398590 | A1* | 12/2024 | Lenzi | A61F 2/66 |

FOREIGN PATENT DOCUMENTS

| | | | | | |
|---|---|---|---|---|---|
| CN | 119367113 | A | * | 1/2025 | A61F 2/68 |
| EP | 2087858 | A1 | * | 8/2009 | A61F 2/70 |
| JP | 2023528509 | A | * | 7/2023 | A61F 2/66 |
| WO | 2020012319 | A1 | | 1/2020 | |

* cited by examiner

3 DEGREES OF FREEDOM ANKLE PROSTHESIS

CROSS REFERENCE TO THE RELATED APPLICATIONS

This application is the national stage entry of International Application No. PCT/TR2021/051642, filed on Dec. 30, 2021, which is based on and claims priority to Turkish Patent Application No. 2020/22500, filed Dec. 30, 2020, the entire contents of which are incorporated herein by reference.

TECHNICAL FIELD

The present invention relates to an ankle prosthesis or orthosis for use in patients with congenital limb loss or amputation.

BACKGROUND

For people with congenital limb loss or patients who have had to lose one or more limbs due to various diseases or accidents, prosthesis technology is one of the most important technologies that enable the patient to maintain a functional life close to normal.

In the state-of-art, there are a number of prosthetic devices for individuals who have had one or both feet amputated or below the knee amputation. These prosthetic devices can be classified as passive prostheses that can store and release energy, microprocessor-controlled prostheses that can adapt to different environments and speeds, and active prostheses that can provide direct positive net power to the ankle.

In the prior art, there are passive prostheses designed only for kinematic walk, without an energy storage in order to perform the movement of the prosthesis and a returning capability to use said energy. The disadvantage of these passive prostheses is that they cause the amputee to exert too much effort to make the movement, and disrupt the gait symmetry. Most of the passive prostheses can only provide movement in the sagittal plane.

Another type of prosthesis in the state of the art, i.e., the prostheses with energy storage and returning capacity, are efficient, but they have a structure that limits the mobility of the user and allows user movements only in the sagittal plane.

Another type of prosthesis in the state of the art are microprocessor-controlled prostheses that can adapt to different walking speeds. These microprocessor-controlled prostheses provide the user with greater adaptability to walking at different speeds and in different environments, but they still consume a significant amount of metabolic effort. They can only perform movements in the sagittal plane. These prostheses are mechanically ineffective, and are moderately heavy and expensive.

Patent application No. WO2020012319 discloses a foot prosthesis including an internal keel and an encapsulation material. Said foot prosthesis is made of two parts, namely an elastic ankle and an elastic blade, to ensure a behavior of the prosthesis as close as possible to the biomechanics of a sound human foot.

Patent application No. US2019307583 describes a prosthetic device including methods of actuating AWLDs by modulating force or torque, power, position, velocity, work, or other control variables or providing feedback to the user in the form of mechanical or electrical stimuli. Said methods are performed in real time and employ integrated, autonomous sensing, microprocessing and actuation systems.

If the state of the art is examined, there is still a need to develop an ankle prosthesis or orthosis that can imitate the movement and energetic behavior of the user's natural ankle joints, which is activated by simply placing a motor therein, when desired and without the need for an electronic controller, and which does not have a cumbersome structure while performing these movements.

SUMMARY

An object of the present invention is to provide an ankle prosthesis or orthosis with three degrees of freedom that is capable of functioning in an active and passive manner, for use in individuals with congenital limb loss or amputation.

An object of the present invention is to provide an ankle prosthesis or orthosis that increases the energy efficiency required for the mobility of an ankle prosthesis or orthosis by storing, preserving and then returning the energy during the movement of said device.

Another object of the present invention is to provide an ankle prosthesis or orthosis that can imitate the movement and energetic behavior of a person's natural ankle joints without requiring an electronic controller in a passive version, which is not a cumbersome while performing these movements.

Another object of the present invention is to activate said passive ankle prosthesis or orthosis by simply adding an actuator therein, and to provide an ankle prosthesis or orthosis with increased energy conversion.

In order to achieve the above objects, the present invention relates to an ankle prosthesis or orthosis including a tibia portion, two upper foot parts to perform the inversion and eversion of the ankle prosthesis or orthosis, wherein the connection with the tibia portion positioned between the two upper foot parts, and with the two upper foot parts is achieved at the right and left sides of the tibia portion by means of the connecting members, and two lower foot parts positioned parallel to each other, wherein the prosthesis or orthosis is in contact with the surface. Said first piston includes at least one balance member and allows alignment of the ankle prosthesis or orthosis with a below-knee mechanism at 0 degrees. The ankle prosthesis or orthosis includes two first pistons positioned parallel to each other at a certain distance in the middle of the two foot parts and including at least one dorsiflexion member that stores kinetic energy during the movement of the ankle prosthesis or orthosis and releases it during the push-off, wherein the lower connecting member of the tibia, which connects the tibia portion with the two first pistons, is connected by the connecting member so as to be disposed between the two first pistons, wherein energy is stored in the dorsiflexion member with the bending movement of the ankle towards the leg during walking, and the stored energy is returned back with the plantar flexion during the push-off, i.e., the movement of the ankle moving away from the leg and towards the surface, and a second piston that connects the rear parts of the two upper foot parts with the rear parts of the two lower foot parts. The second piston includes a heel member located therein, on which pressure is exerted by the downward movement of the piston and which allows inversion and eversion of the ankle prosthesis or orthosis to be performed.

In order to achieve the above purposes, the present invention relates to an ankle prosthesis or orthosis in which the tibia portion also includes a torsion member positioned between the two upper and lower parts of the tibia portion to perform an internal rotational movement of the ankle prosthesis or orthosis.

In order to achieve the above objects, the present invention relates to an ankle prosthesis or orthosis in which the torsion member is a torsion spring.

In order to achieve the above objects, the present invention relates to an ankle prosthesis or orthosis in which the upper surface of the upper foot part consists of two identical parts with an outward elliptical form.

In order to achieve the above objects, the present invention relates to an ankle prosthesis or orthosis on which the upper foot part includes at least one lightening space at certain intervals.

In order to achieve the above objects, the present invention relates to an ankle prosthesis or orthosis provided with a balancing spring housing positioned on the upper foot part.

In order to achieve the above objects, the present invention relates to an ankle prosthesis or orthosis that encloses the tibia portion and includes a foot clamping member with a balancing spring thereon.

In order to achieve the above objects, the present invention relates to an ankle prosthesis or orthosis wherein the balancing spring is inserted into the balancing spring housing located on the upper foot part.

In order to achieve the above objects, the present invention relates to an ankle prosthesis or orthosis in which the heel member is a heel spring.

In order to achieve the above objects, the present invention relates to an ankle prosthesis or orthosis including at least one actuator to provide the kinetic energy required for movement of the ankle prosthesis or orthosis.

In order to achieve the above objects, the present invention relates to an ankle prosthesis or orthosis in which the actuator is positioned within the tibia portion.

LIST OF REFERENCES

Figure 1:
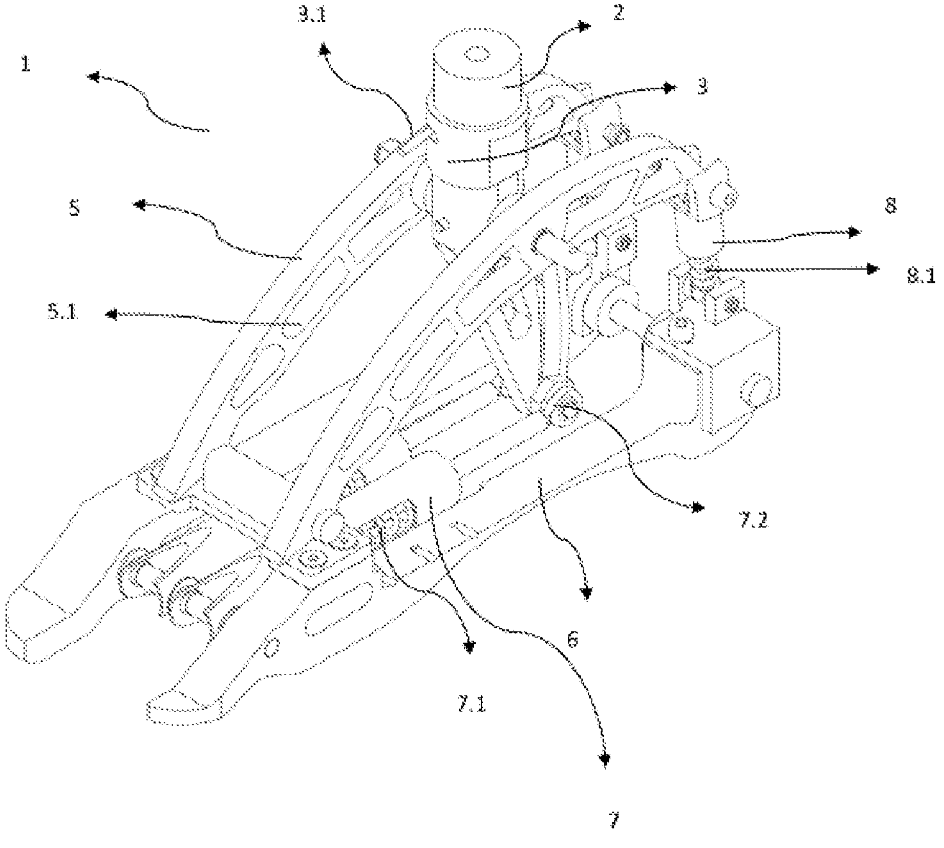
FIG. 1 is a top perspective view of an ankle prosthesis or orthosis.
Figure 2:
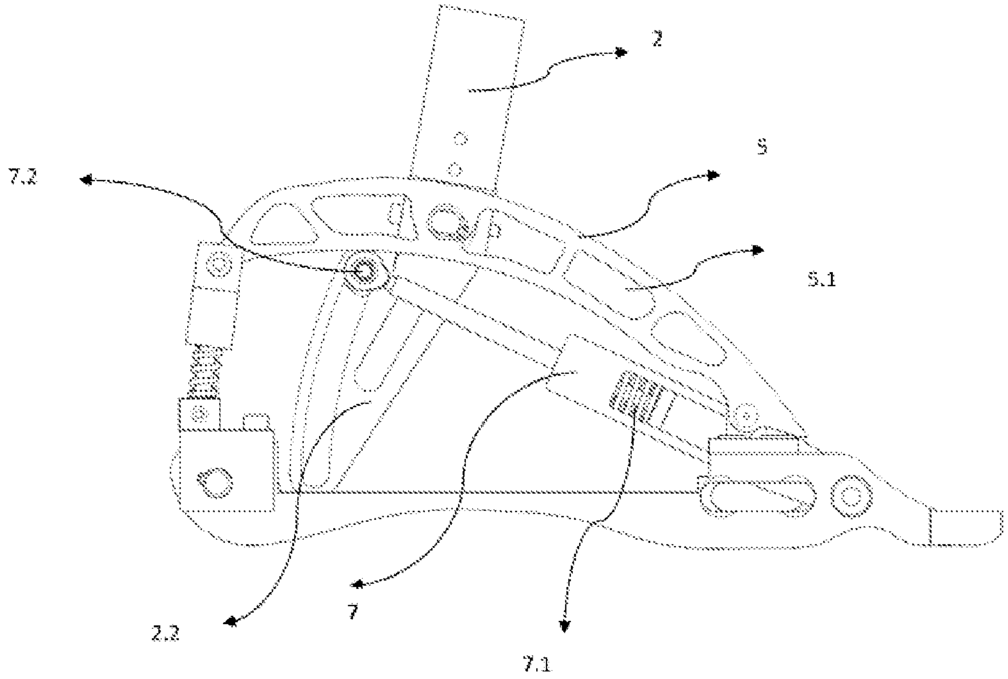
FIG. 2 is a side perspective view of the ankle prosthesis or orthosis with the first piston being visible.
Figure 3:
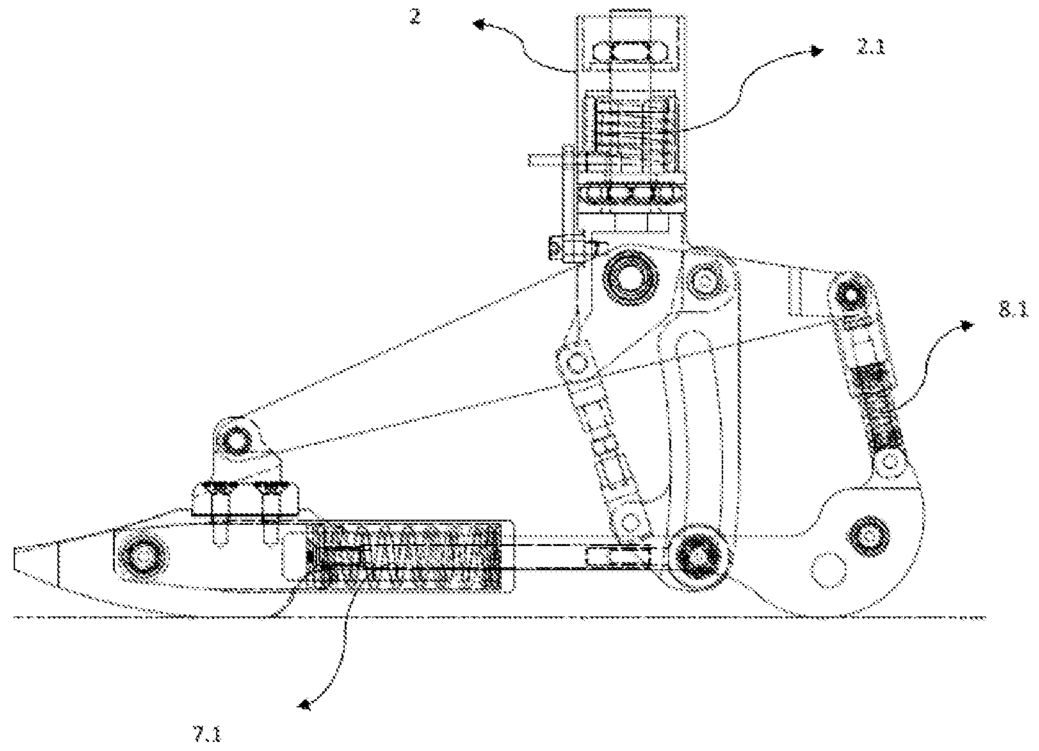
FIG. 3 is a side perspective view of the torsion member, dorsiflexion member and heel member of the ankle prosthesis or orthosis.
Figure 4:
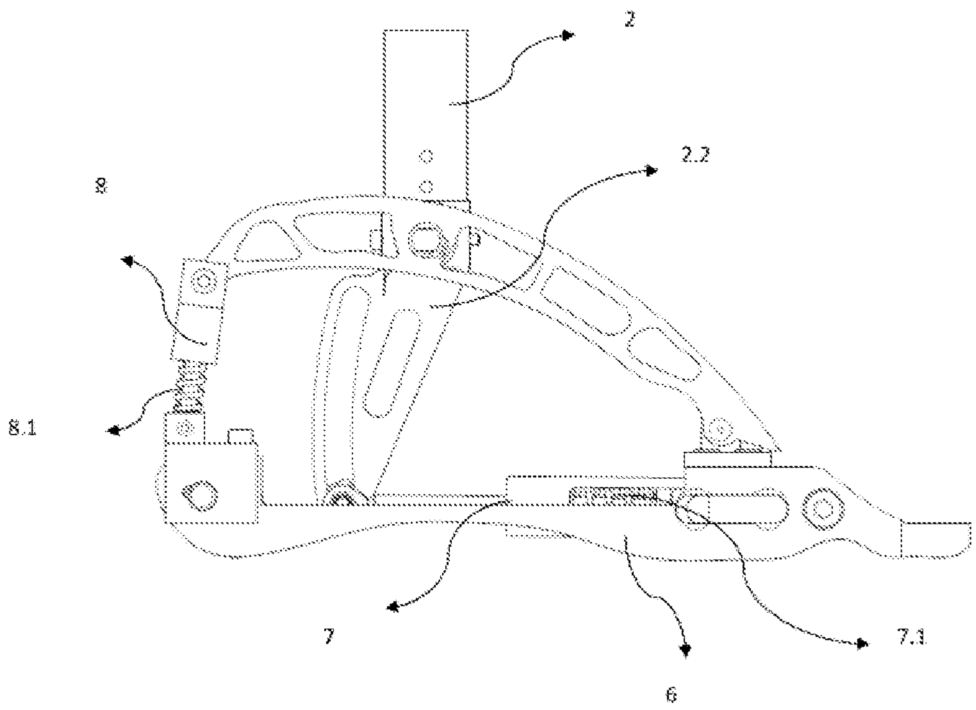
FIG. 4 is a side perspective view of the ankle prosthesis or orthosis.
Figure 5:
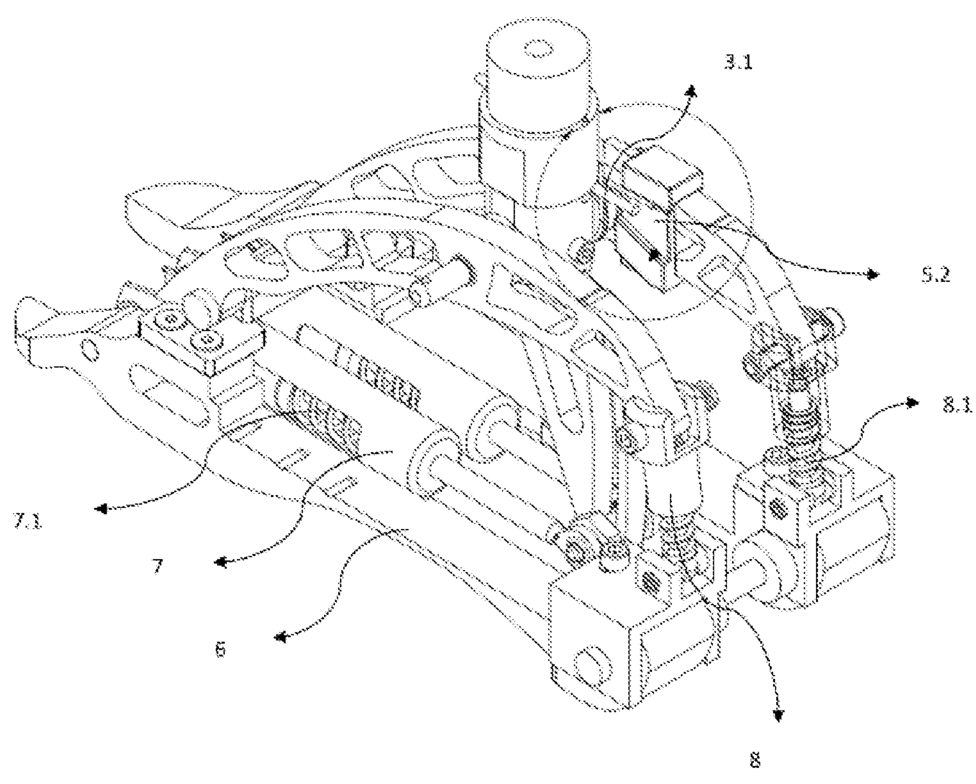
FIG. 5 is a rear top perspective view of the ankle prosthesis or orthosis.
Figure 6:
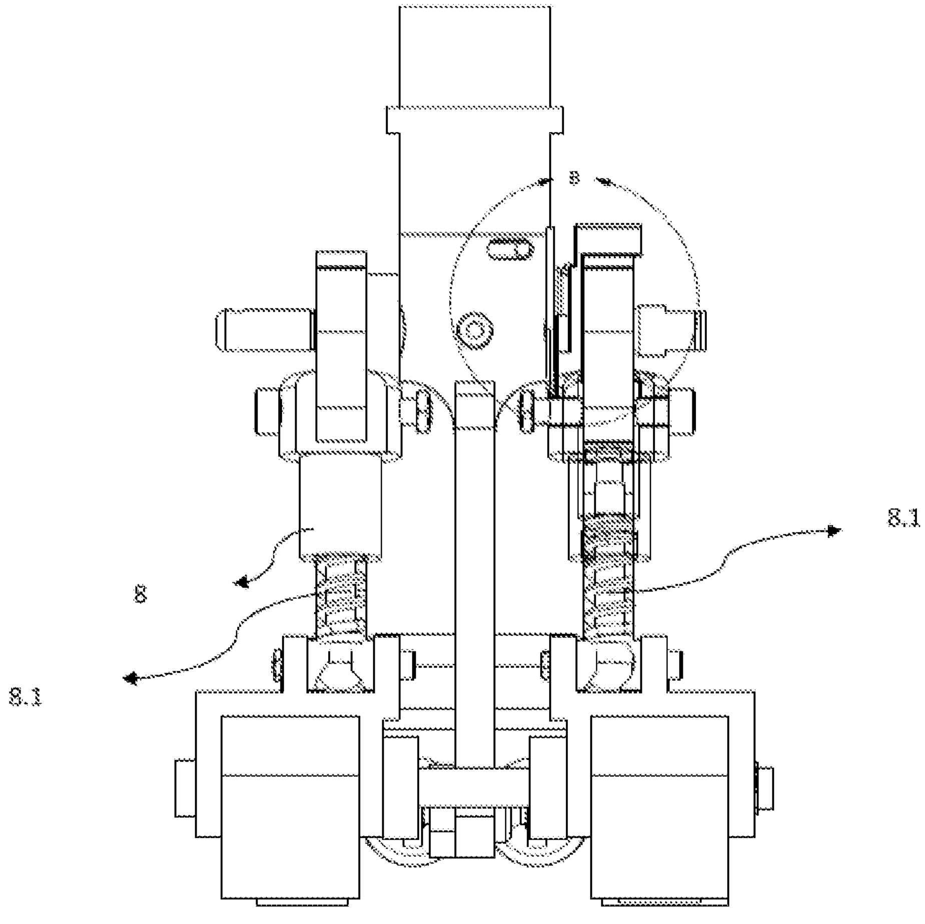
FIG. 6 is a rear perspective view of the ankle prosthesis or orthosis.

- 1. Ankle prosthesis or orthosis
- 2. Tibia portion
  - 2.1 Torsion member
  - 2.2 Tibia connecting member
- 3. Foot clamping member
  - 3.1 Balancing spring
- 5. Upper foot part
  - 5.1. Lightening space
  - 5.2 Balancing spring housing
- 6. Lower foot part
- 7. First piston
  - 7.1 Dorsiflexion member
  - 7.2 Piston connecting member
- 8. Second piston
  - 8.1 Heel member

DETAILED DESCRIPTION OF THE EMBODIMENTS

The present invention relates to a multi-functional ankle prosthesis or orthosis (1) for use in individuals with congenital limb loss or amputation.

The ankle prosthesis or orthosis (1) of the invention allows the user to perform the movements and kinetic behaviors of the ankle joints in three cardinal planes, i.e., sagittal, transverse and frontal planes, in an energy efficient manner. With the three cardinal plane movements, the present invention performs natural and effective push-off, which is one of the most important functions of the ankle joint.

In a main embodiment of the invention, there is disclosed is a multi-functional ankle prosthesis or orthosis (1) capable of performing inversion and eversion and dorsiflexion plantarflexion movements in three cardinal planes, namely sagittal, transverse and frontal planes.

In the main embodiment of the invention, the ankle prosthesis or orthosis (1) includes a tibia portion (2), a foot clamping member (3), at least one upper foot part (5), at least one lower foot part (6), at least a first piston (7), and at least a second piston (8).

In the main embodiment of the invention, the tibia portion (2) provides the connection with the below-knee limb or mechanism. It includes a torsion member (2.1) disposed between the tibia portion (2), and a tibia connecting member (2.2) which is integral with the tibia portion (2), and connecting the tibia portion (2) with the at least a first piston (7) by means of the piston connecting member (7.2). Said torsion member (2.1) is positioned between the two lower and upper parts of the tibia portion (2). Said torsion member (2.1) performs the internal rotational movement of the ankle prosthesis or orthosis (1), which is one of the three cardinal plane movements, i.e., the rotation movement.

In the main embodiment of the invention, the tibia portion (2) has a cylindrical form and is configured to be hollow.

In the main embodiment of the invention, the torsion member (2.1) is a torsion spring.

In the main embodiment of the invention, the torsion member (2.1) may be consisted of such elements as different connecting elements and spring types such as piston, shaft, etc., capable of generating a force similar to the force provided by the internal rotational movement and the compression movement.

In the main embodiment of the invention, the foot clamping member (3) includes a balancing spring (3.1). Said balancing spring (3.1) is inserted into the balancing spring housing (5.2) located at the upper foot part (5). With the movement of said balancing spring (3.1), the ankle prosthesis or orthosis (1) is aligned at 0 degrees in the sagittal plane.

In an embodiment of the invention, the ankle prosthesis or orthosis (1) includes two identical upper foot parts (5).

In the main embodiment of the invention, ankle prosthesis or orthosis (1) includes two identical upper foot parts (5), the upper surface of which has an outward elliptical form. The upper foot part (5) can rotate independently. In this way, it performs the inversion and eversion of the ankle prosthesis or orthosis (1), which are one of the three coronal plane movements. The upper foot part (5) includes at least one lightening space (5.1) located thereon at certain intervals. Said lightening spaces (5.1) ensure that the ankle prosthesis or orthosis (1) is greatly lightened and has an ergonomic structure.

In the main embodiment of the invention, the connection with the tibia portion (2) and the upper foot part (5) is provided by means of the connecting members at the right and left sides of the tibia portion (2).

In the main embodiment of the invention, the ankle prosthesis or orthosis (1) includes at least one lower foot part (6) formed in the form of a human foot sole, having a horizontal and flat surface where the prosthesis or orthosis comes into contact with the surface. In the main embodiment of the invention, the lower foot part (6) consists of two identical horizontal flat surfaces positioned parallel to each other, one on the right side and the other on the left side.

In the main embodiment of the invention, at least a first piston (7) is positioned in the middle of the two lower foot parts (6), which are positioned parallel to each other in the said right and left parts. Said first piston (7) includes at least one dorsiflexion member (7.1) that stores kinetic energy during the movement of the ankle prosthesis or orthosis (1) and releases it during push-off.

In the basic embodiment of the invention, two first pistons (7) that are parallel and identical to each other are positioned in the middle of the two lower foot parts (6), which are positioned as described above, at a certain distance from each other.

In the basic embodiment of the invention, energy is stored in the dorsiflexion member (7.1) with the dorsiflexion movement during walking, i.e., with the bending movement of the ankle towards the leg. The stored energy is returned back by the plantar flexion movement during the push-off, i.e., the movement of the ankle away from the leg towards the surface. After the ankle prosthesis or orthosis (1) completes its dorsiflexion, the position of the dorsiflexion member (7.1) is changed on a pre-calculated trajectory (a trajectory in which the dorsiflexion member (7.1) does not release its energy). In this way, energy is returned back in the angle range of plantarflexion motion. Said trajectory is a trajectory calculated such that the length of the dorsiflexion member (7.1) does not change, i.e., no energy is charged thereon. In practice, in order for the sliding movement to take place (since there is friction), a very small part of the energy in the dorsiflexion member (7.1) is spent in this movement.

In the main embodiment of the invention, the dorsiflexion member (7.1) is a dorsiflexion spring. Still, in a basic embodiment of the invention, the energy of the dorsiflexion spring compressed in dorsiflexion, where the ankle prosthesis or orthosis (1) has an angle of 10 degrees with the leg, is returned back by the plantarflexion movement where the ankle prosthesis or orthosis (1) makes the full-plantar flexion angle at the end of push-off. In this way, one-to-one correspondence with the working principle of the biological ankle is obtained.

In the main embodiment of the invention, the dorsiflexion member (7.1) is a dorsiflexion spring.

In other preferred embodiments of the invention, the dorsiflexion member (7.1) may be consisted of such elements as different connecting elements and spring types capable of generating a force similar to the force provided by the compression movement.

In the main embodiment of the invention, the passive ankle prosthesis or orthosis (1) performs the push-off movement with the energy stored in the dorsiflexion spring. With the addition of an actuator in the passive ankle prosthesis or orthosis (1), push-off can be achieved with full energy.

Another end of the tibia connecting member (2.2) that does not connect with the foot clamping member (3) of the tibia portion (2) is mounted by means of the piston connecting member (7.2) such that it is also located in the middle of the ends of the two first pistons (7) positioned parallel to each other. The other end of the two first pistons (7) positioned in the inner part of the lower foot parts (6), which are positioned parallel to each other, that are not connected with the tibia connecting member (2.2), are mounted on the front inner surfaces of the lower foot parts (6) by means of the connecting members.

In the main embodiment of the invention, the assembly of the front parts of the two upper foot parts (5) to the front parts of the two lower foot parts (6) is carried out by means of connecting members. The connection of the rear parts of the two upper foot parts (5) and the rear parts of the two lower foot parts (6) is carried out by means of a second piston (8). Said second piston (8) includes a heel member (8.1) positioned therein. The second piston (8) can move upwards and downwards. With the downward movement of the second piston (8), pressure is applied on the heel member (8.1) and energy is stored. The heel member (8.1) allows inversion and eversion of the ankle prosthesis or orthosis (1) to be performed.

In the main embodiment of the invention, the heel member (8.1) is a heel spring.

In other preferred embodiments of the invention, the heel member (8.1) may be consisted of such elements as different connecting elements and spring types capable of generating a force similar to the force provided by the compression movement.

In the main embodiment of the invention, energy is stored in the dorsiflexion spring and heel spring in the gait cycle and is finally returned back during the push-off to move the body forward. The heel spring is a spring used to ensure that the foot strikes the ground softly.

In the meantime, in order to fulfill the natural functions of the ankle, the balancing spring (3.1) (the function of pulling to 0 degrees after plantarflexion during the push-off in the sagittal plane) and the torsion spring (2.1) (resetting function after inversion in the transverse plane) also store and release energy to perform the natural movement of the ankle.

In an embodiment of the invention, the kinetic energy required for the movement of the ankle prosthesis or orthosis (1) is provided by an actuator to support the dorsiflexion member (7.1). In an embodiment of the invention where the kinetic energy is provided by the actuator, the main elements described in the main embodiment of the invention are also included. Said actuator is positioned in the space inside the tibia portion (2) in cylindrical form. In an embodiment of the invention, said actuator is a motor.

What is claimed is:

1. An ankle prosthesis or orthosis comprising a tibia portion, two upper foot parts to perform inversion and eversion movements of the ankle prosthesis or orthosis, wherein the tibia portion is positioned between the two upper foot parts, and connected with the two upper foot parts at right and left sides of the tibia portion by means of connecting members, and two lower foot parts, wherein the two lower foot parts are positioned parallel to each other, wherein the ankle prosthesis or orthosis is in contact with a support surface, comprising two first pistons, wherein the two first pistons are positioned parallel to each other at a predetermined distance at a middle of the two lower foot parts and comprise at least one dorsiflexion member, wherein the at least one dorsiflexion member stores kinetic energy during a movement of the ankle prosthesis or orthosis and releases the kinetic energy during push-off, wherein a tibia connecting member is connected by a piston connecting member, wherein the tibia connecting member connects the tibia portion with the two first pistons, wherein the tibia connecting member is disposed between the two first pistons, wherein the at least one dorsiflexion member stores energy during dorsiflexion of the ankle prosthesis or orthosis toward a user's leg during walking, and returns the stored energy during plantarflexion as the ankle prosthesis or orthosis moves away from the user's leg toward the support surface, and two second pistons, wherein the two second pistons connect rear parts of the two upper foot parts with rear parts of the two lower foot parts, wherein each second piston includes a heel member located therein, wherein a pressure is exerted on the heel member by a downward movement of the respective second piston, and the heel member allows inversion and eversion of the ankle prosthesis or orthosis to be performed.

2. The ankle prosthesis or orthosis according to claim 1, wherein the tibia portion further comprises a torsion member, wherein the torsion member is positioned between two lower and two upper parts of the tibia portion and the torsion member performs an internal rotational movement of the ankle prosthesis or orthosis.

3. The ankle prosthesis or orthosis according to claim 2, wherein the torsion member is a torsion spring.

4. The ankle prosthesis or orthosis according to claim 3, wherein each of the two upper foot parts comprises two identical parts, and an upper surface having an outward elliptical form.

5. The ankle prosthesis or orthosis according to claim 3, wherein each of the two upper foot parts comprises at least one lightening space located thereon at predetermined intervals.

6. The ankle prosthesis or orthosis according to claim 3, wherein each of the two upper foot parts comprises a balancing spring housing positioned thereon.

7. The ankle prosthesis or orthosis according to claim 2, wherein each of the two upper foot parts comprises two identical parts, and an upper surface having an outward elliptical form.

8. The ankle prosthesis or orthosis according to claim 2, wherein each of the two upper foot parts comprises at least one lightening space located thereon at predetermined intervals.

9. The ankle prosthesis or orthosis according to claim 2, wherein each of the two upper foot parts comprises a balancing spring housing positioned thereon.

10. The ankle prosthesis or orthosis according to claim 1, wherein each of the two upper foot parts comprises two identical parts, and an upper surface having an outward elliptical form.

11. The ankle prosthesis or orthosis according to claim 10, wherein each of the two upper foot parts comprises at least one lightening space located thereon at predetermined intervals.

12. The ankle prosthesis or orthosis according to claim 10, wherein each of the two upper foot parts comprises a balancing spring housing positioned thereon.

13. The ankle prosthesis or orthosis according to claim 1, wherein each of the two upper foot parts comprises at least one lightening space located thereon at predetermined intervals.

14. The ankle prosthesis or orthosis according to claim 13, wherein each of the two upper foot parts comprises a balancing spring housing positioned thereon.

15. The ankle prosthesis or orthosis according to claim 1, wherein each of the two upper foot parts comprises a balancing spring housing positioned thereon.

16. The ankle prosthesis or orthosis according to claim 1, comprising a foot clamping member, wherein the foot clamping member encloses the tibia portion and has a balancing spring thereon.

17. The ankle prosthesis or orthosis according to claim 16, wherein the balancing spring is inserted into a balancing spring housing located on each of the two upper foot parts.

18. The ankle prosthesis or orthosis according to claim 1, wherein the heel member is a heel spring.

19. The ankle prosthesis or orthosis according to claim 1, comprising at least one actuator to provide the kinetic energy required for the movement of the ankle prosthesis or orthosis.

20. The ankle prosthesis or orthosis according to claim 19, wherein the at least one actuator is positioned inside the tibia portion.

* * * * *